United States Patent
Wood et al.

(10) Patent No.: US 6,571,643 B1
(45) Date of Patent: Jun. 3, 2003

(54) ULTRASOUND SPEED MEASUREMENT OF TEMPERATURE AND PRESSURE EFFECTS

(75) Inventors: Robert P. Wood, San Carlos, CA (US); Serge Plotkin, Belmont, CA (US); Jacob Harel, San Francisco, CA (US); Alfred Samson Hou, Sunnyvale, CA (US)

(73) Assignee: Electronics for Imaging, Inc., Foster City, CA (US)

( * ) Notice: Subject to any disclaimer, the term of this patent is extended or adjusted under 35 U.S.C. 154(b) by 0 days.

(21) Appl. No.: 09/574,567

(22) Filed: May 17, 2000

Related U.S. Application Data

(63) Continuation-in-part of application No. 09/134,315, filed on Aug. 13, 1998, now Pat. No. 6,118,205.

(51) Int. Cl.[7] ................................................. G01F 1/66
(52) U.S. Cl. ..................................... 73/861.27; 73/597
(58) Field of Search .............................. 73/597, 861.18, 73/861.25, 861.27, 861.28, 861.29, 861.31

(56) References Cited

U.S. PATENT DOCUMENTS

| | | | |
|---|---|---|---|
| 3,432,691 A | 3/1969 | Shoh | |
| 3,622,899 A | 11/1971 | Elsenburg | 330/22 |
| 3,689,781 A | 9/1972 | Kawada | 310/8.1 |
| 3,691,410 A | 9/1972 | Kawada | 310/8.1 |
| 3,694,713 A | 9/1972 | Duren et al. | 318/116 |
| 3,708,701 A | 1/1973 | Kawada | 310/8.1 |
| 3,819,961 A | 6/1974 | Bourgeois et al. | 310/8.1 |
| 3,824,447 A | 7/1974 | Kuwabara | 321/15 |
| 3,900,800 A | 8/1975 | Maltz | 330/15 |
| 3,975,650 A | 8/1976 | Payne | 310/8.1 |
| 4,053,821 A | 10/1977 | Hose, Jr. et al. | 363/60 |
| 4,054,806 A | 10/1977 | Moriki et al. | 310/318 |
| 4,070,589 A | 1/1978 | Martinkovic | 307/246 |
| 4,112,756 A | 9/1978 | MacLennan et al. | |
| 4,262,545 A * | 4/1981 | Lamarche et al. | 73/861.27 |
| 4,625,137 A | 11/1986 | Tomono | |
| 4,963,703 A | 10/1990 | Phillips et al. | 178/19 |
| 5,073,878 A | 12/1991 | Gilchrist | 367/137 |
| 5,437,194 A * | 8/1995 | Lynnworth | 73/861.27 |

FOREIGN PATENT DOCUMENTS

| | | |
|---|---|---|
| DE | 031 50 011 A1 | 6/1983 |
| DE | 196 17 961 A1 | 11/1997 |

* cited by examiner

Primary Examiner—Richard A. Moller

(57) ABSTRACT

An apparatus and process for using ultrasound to measure speed and acceleration in fluids is provided. Three preferred embodiments are disclosed. The first preferred embodiment measures fluid velocity, such as, for example, wind, under standard atmospheric pressure-temperature. The second preferred embodiment measures gas velocity, such as, for example, wind, affected by and automatically calibrates for pressure-temperature. The third preferred embodiment measures gas density, such as, for example, density altitude. Applications of the invention include wind direction and speed calculation in agriculture, aviation, hydraulics, and other industries. One of the advantages provided by the invention is there are no moving parts in making such measurements.

6 Claims, 3 Drawing Sheets

ULTRASOUND SPEED MEASUREMENT OF TEMPERATURE AND PRESSURE EFFECTS

This is a continuation-in-part of U.S. patent application Ser. No. 09/134,315, filed August 13, 1998 now U.S. Pat. No. 6,118,205.

BACKGROUND OF THE INVENTION

1. Technical Field

The invention relates to measurement of speed and acceleration of fluids. More particularly, the invention relates to an ultrasound technology, disclosed in U.S. patent application Ser. No. 09/134,315 , filed Aug. 14, 1998.

2. Description of the Prior Art

The speed of sound in air along a line or path between any two points may be determined by measuring the time taken for the sound to travel between the two points. With the air moving from one point to the other, sound travelling in the same direction is speeded up, while sound travelling in the other direction is slowed down. Where the actual wind has a speed W in a direction which is at an angle $\theta$ to the sound speed line, then the wind component along that line is $W \cos \theta$, and the wind component along a line that is perpendicular to the sound speed line is $W \sin \theta$. In such a case, the sound speed S along the line is $S_o + W \cos \theta$, where $S_o$ is the sound speed in still air. If the distance over which the sound speed is being measured is D, then the time T taken is D/S. Thus, $T = D/(S_o + W \cos \theta)$.

M. C. Heard, Wind Speed Measurement, U.S. Pat. No. 4,336,606 (Jun. 22, 1982) discloses an apparatus for and a method of detecting and measuring wind gradient at a location, and involves a comparison of the wind speed in the same direction at two or more heights at the location. Said comparison based upon a comparison of the ;speed of sound in a direction and at specific heights, a difference in the apparent speeds indicating the presence of wind gradient. The disclosure involves: beaming a regular sound wave train between a transmitter/receiver pair positioned and like orientated at each of two or more heights at the location; noting each transceiver pair's received sound wave train phase, and comparing it with its transmitted phase, so as to deduce the wind-caused phase change; and using these deduced phase changes to calculate the actual wind speeds, and thus the relative changes of wind speed with height, in the selected direction.

The disclosed apparatus has the transmitter/receiver pairs positioned at too great a distance (approximately 200 feet) for the measurement to be effective and accurate. In addition, applying the teachings to an airplane landing situation is not practical as the noise level of an incoming plane is too large and will interfere with the accurate and timely measurements of the ultrasound transmissions.

M. J. Gill, Speed Measurement Device, U.S. Pat. No. 5,163,331 (Nov. 17, 1992) discloses a fluid speed measurement device that includes a pair of ultrasonic transducers spaced in a measuring chamber. A transmitter and receiver system is controlled by a microprocessor which generates pulses which periodically invert and these are switched by switches that allow alternate direction of transmission. Reception and detection of signals is effected by particular blocks. Time calculation is determined by a counter and results are used to calculate flow speed or volume using a microprocessor. A speed increase in the measurement region is effected using a venturi device.

The device disclosed in Gill is a closed device. In a closed configuration the speed of a gas is higher, than the speed of the same gas in an open configuration. The disclosed system therefore is not required to be sufficiently sensitive to detect signals in such a fluid wherein the speed is not so high, as in, for example, the atmosphere.

Hermann et al, Method and Circuit Arrangement for the Measurement of Flow Speed by Means of Acoustical Transit Time Differences, U.S. Pat. No. 5,804,739 (Sep. 8, 1998) discloses a "method of determining the time point ($t_0$) of the start of a high frequency oscillation packet triggered as a result of a corresponding external excitation which is extremely tolerant relative to systematic disturbances from various sources that consists of determining the times at at least two points of the envelope curve of the oscillation packet with respect to an arbitrary zero time point. Of these two points one is a characteristic point of the envelope curve and the other has an amplitude equal to a predetermined fraction of the amplitude at the characteristic envelope curve point. It is preferable that during " . . . calculation the angle between the directions of the ultrasonic pulse packets and the flow direction of the medium, . . . differs significantly from 90 degree, is particularly taken into account."

Hermann et al does not disclose nor suggest automatic calibration for pressure-temperature, nor portability, no that the size of the measuring device be of a relative small size.

It would advantageous to provide a fluid speed measurement apparatus along with a process that takes digital measurements so as to be more precise.

It would advantageous to provide a fluid speed measurement apparatus along with a process that uses a protective, ventilated material, such as, for example, a lightweight plastic, so as to allow for automatic calibration to pressure-temperature.

It would advantageous to provide a fluid speed measurement apparatus along with a process that, is small enough and portable to be used at an airplane runway for measuring wind velocity and direction, yet placed far enough away from the runway so that loud airplane noises cannot interfere with the measurement apparatus and process.

It would advantageous to provide a fluid speed measurement apparatus along with a process that has no moving parts, such as, for example, a ventilator or moving flap used in detecting fluid speed.

SUMMARY OF THE INVENTION

An apparatus and process for using ultrasound technology disclosed in U.S. Ser. No. 09/134,315 pursuant to the Whiteboard project, to measure speed and acceleration in fluids, are provided. Three preferred embodiments are disclosed. The first preferred embodiment measures fluid velocity, such as, for example, wind, under standard atmospheric pressure-temperature. The second preferred embodiment measures fluid velocity, such as, for example, wind, affected by and automatically calibrates for pressure and temperature. The third preferred embodiment measures gas or air density, such as, for example, density altitude. Applications of the invention include wind direction and speed calculation in agriculture, aviation, hydraulics, and other industries. One of the advantages provided by the invention is there are no moving parts in making such measurements.

DETAILED DESCRIPTION OF THE INVENTION

An apparatus and process for using ultrasound technology disclosed in U.S. Ser. No. 09/134,315 pursuant to the Whiteboard project, to measure speed and acceleration in fluids are provided. Three preferred embodiments are disclosed. The first preferred embodiment measures fluid velocity, such as, for example, wind, under standard atmospheric pressure and temperature. The second preferred embodiment measures fluid velocity, such as, for example, wind, affected by and automatically calibrates for pressure and temperature. The third preferred embodiment measures fluid density, such as, for example, density altitude. Applications of the invention include wind direction and speed calculation in agriculture, aviation, hydraulics, and other industries. One of the advantages provided by the invention is there are no moving parts in making such measurements.

Figure 1:
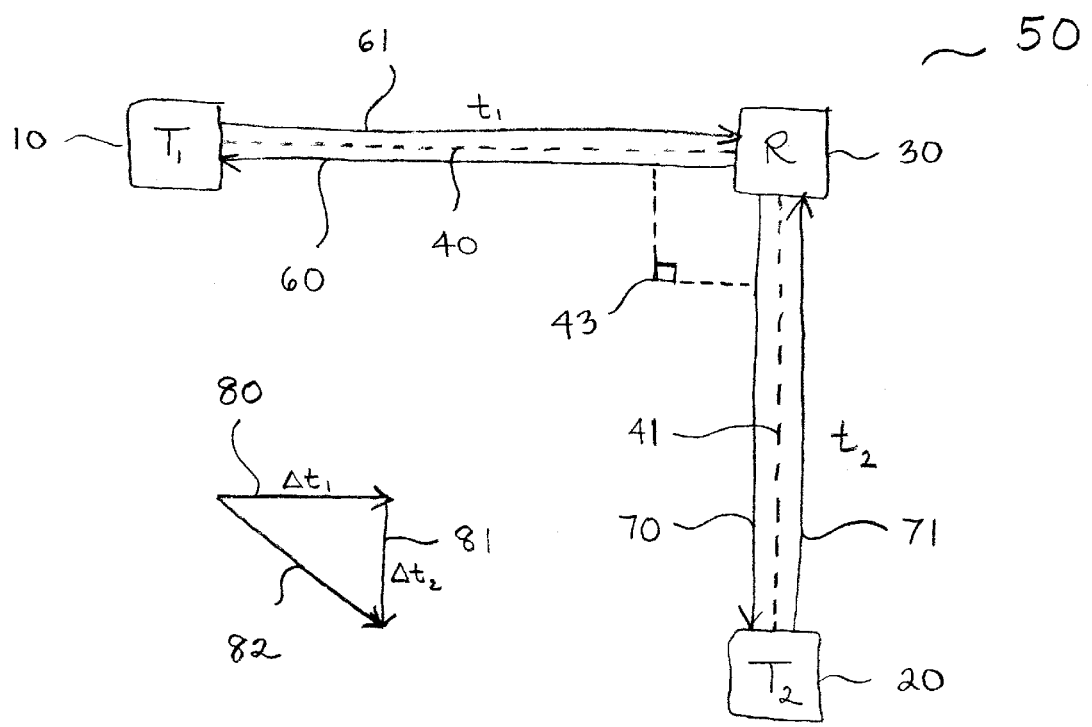
FIG. 1 is a diagram of the first preferred embodiment, according to the invention.

FIG. 1 is a diagram of a first preferred embodiment of an apparatus for calculating a wind velocity vector in standard atmospheric pressure. A first transmitter element 10, $T_1$, is adapted to transmit ultrasonic pulses. A second transmitter element 20, $T_2$, is also adapted to transmit ultrasonic pulses. A receiver element 30 is adapted to receive ultrasonic pulses. The first transmitter 10 is positioned a relatively short distance 40 of about 2 feet from the receiver 30. The second transmitter 20 is also positioned a short distance 41 of about 2 feet from the receiver 30 and positioned at a 90 degree angle 43 from the first transmitter 10. The first transmitter 10, the second transmitter 20, and the receiver 30 are placed in an open configuration 50.

The time transit vector 60 of a generic ultrasonic pulse from the receiver 30 to the first transmitter 10 in standard atmospheric pressure with no wind is a predetermined entity. Similarly, the time transit vector 70 of a generic ultrasonic pulse from the receiver 30 to the second transmitter 20 in standard atmospheric pressure with no wind is a predetermined entity. A time transit vector 61, $t_1$, from the first transmitter 10 to the receiver 30 is calculated. A second time transit vector 71, $t_2$, from the second transmitter 20 to the receiver 30 is calculated.

A first transit time differential vector 80 is determined by taking the difference between the first transit time vector 61 and the predetermined transit time vector 60 of the generic ultrasonic pulse in standard atmospheric pressure. Similarly, a second transit time differential vector 81 is determined by taking the difference between the second transit time vector 71 and the predetermined transit time vector 70 of the generic ultrasonic pulse in standard atmospheric pressure.

A resultant fluid velocity vector 82 is determined by combining the first transit time differential vector 80 and the second transit time differential vector 81.

Figure 2:
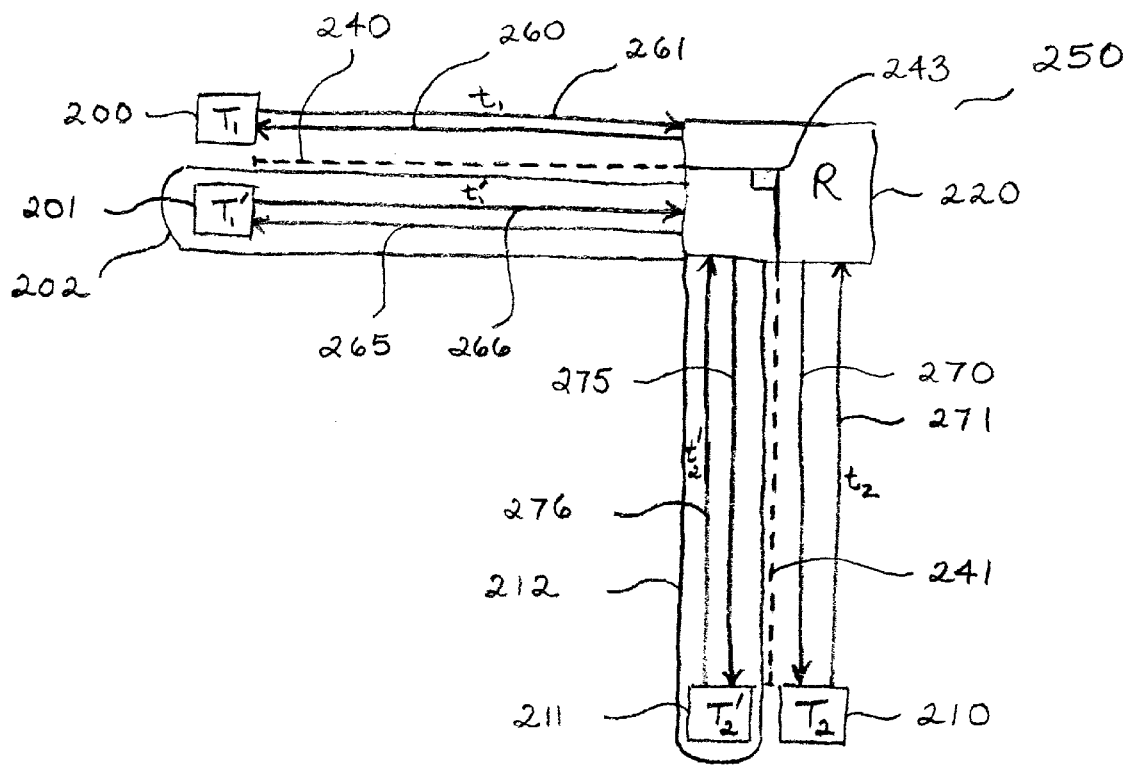
FIG. 2 is a diagram of the second preferred embodiment, according to the invention.
Figure 2:
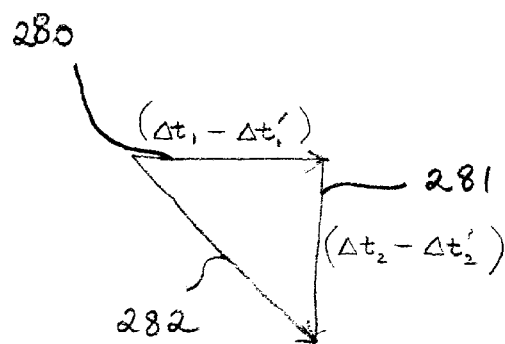

FIG. 2 is a diagram of a second preferred embodiment of an apparatus for calculating an automatically calibrated fluid velocity vector in external pressure-temperature. A first transmitter element 200 is adapted to transmit ultrasonic pulses, and a first transmitter primed element 201 is adapted to transmit ultrasonic pulses. The first transmitter element 200 is placed in an open configuration 250 and the first transmitter primed element 201 is placed in a ventilated tube 202. The first transmitter primed element 201 is positioned along a vertical axis of the first transmitter element 200.

A second transmitter element 210 is adapted to transmit ultrasonic pulses, and a second transmitter primed element 211 is adapted to transmit ultrasonic pulses. The second transmitter element 210 is placed in the open configuration 250 and the second transmitter primed element 211 is placed in a second ventilated tube 212. The second transmitter primed element 211 is positioned along a second axis of the second transmitter element 210, wherein the second axis is perpendicular to the first axis.

A receiver element 220 is adapted to receive ultrasonic pulses from the first transmitter 200, the first transmitter primed 201, the second transmitter 210, and the second transmitter primed 211. The first transmitter 200 and the first transmitter primed 201 are each positioned a first short distance 240 from the receiver 220. The second transmitter 210 and the second transmitter primed 211 are each positioned a second short distance 241 from the receiver 220, and are each positioned at a 90 degree angle from 243 the first transmitter 200 and the first transmitter primed 201.

A time transit vector 260 of an ultrasonic pulse from the receiver 220 to the first transmitter 200 in the open configuration 250 is a predetermined entity. A time transit vector 265 of an ultrasonic pulse from the receiver 220 to the first transmitter primed 201 in the ventilated tube is a predetermined entity. Similarly, a time transit vector 270 of an ultrasonic pulse from the receiver 220 to the second transmitter 210 in the open configuration 250 is a predetermined entity. A time transit vector 275 of an ultrasonic pulse from the receiver 220 to the second transmitter primed 211 in the ventilated tube is a predetermined entity.

An ultrasonic time transit vector 261, $t_1$, from the first transmitter 200 to the receiver 220 is calculated. An ultrasonic time transit vector 266, $t_1$, from the first transmitter primed 201 to the receiver 220 is calculated. Similarly, a second ultrasonic time transit vector 271, $t_2$, from the second transmitter 210 to the receiver 220 is calculated. A second ultrasonic time transit primed vector 276, $t_2$, from the second transmitter primed 211 to the receiver 220 is calculated.

A first transit time differential vector, $\Delta t_1$, by taking the difference between the calculated first transit time vector 261 and the predetermined time transit vector 260 is calculated. A first transit time differential vector primed, $\Delta t_1$, by taking the difference between the calculated first transit time vector primed 266 and the predetermined time transit vector primed 265 is calculated. Similarly, a second transit time differential vector, $\Delta t_2$, by taking the difference between the calculated second transit time vector 271 and the predetermined time transit vector 270 is calculated. A second transit time differential vector primed, $\Delta t_2$, by taking the difference between the calculated second transit time vector primed 276 and the predetermined time transit vector primed 275 is calculated.

A first automatically calibrated fluid velocity component vector 280 is determined by taking the difference between the first transit time differential vector, $\Delta t_1$, and the first transit time differential vector primed, $\Delta t_1$. Similarly, a second automatically calibrated fluid velocity component vector 281 is determined by taking the difference between the second transit time differential-vector, $\Delta t_2$, and the second transit time differential vector primed, $\Delta t_2$.

A resultant automatically calibrated fluid velocity vector 282 is determined by combining the component vectors, 280 and 281.

Figure 3:
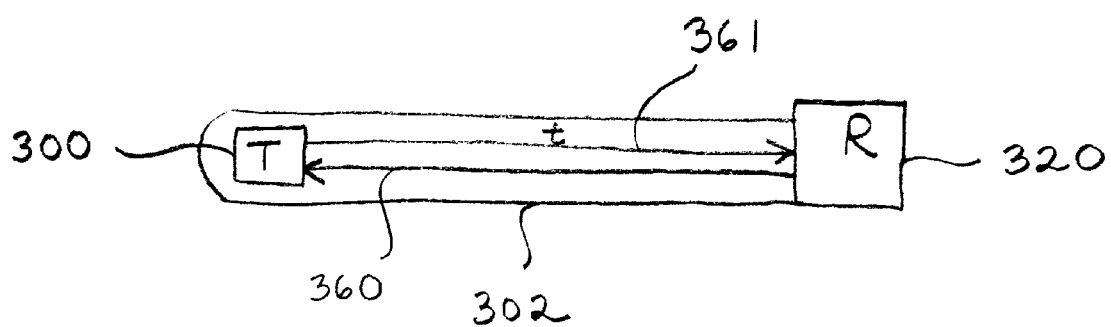
FIG. 3 is a diagram of the third preferred embodiment, according to the invention.

FIG. 3 is a diagram of a third preferred embodiment of an apparatus for calculating density measurement in external pressure-temperature.

A transmitter element 300, T, is adapted to transmit ultrasonic pulses and placed in a ventilated tube 302. A receiver element 320 is adapted to receive ultrasonic pulses. The tubed transmitter 300 is positioned a short distance the receiver 320.

An ultrasonic pulse is transmitted from the tubed transmitter 300 to the receiver 320 and a transit time 361 for the pulse to reach the receiver 320 is calculated.

A transit time differential measurement by taking a difference between the calculated transit time 361 and a predetermined transit time 360 of a generic ultrasonic pulse transmitted from the receiver 320 to the first transmitter 300 in standard atmospheric pressure.

A density measurement is determined from the transit time differential measurement.

It should be appreciated that the first two embodiments work particularly well when the fluid whose speed is calculated is wind. The third embodiment works particularly well for calculating density altitude.

It should be noted that all three preferred embodiments are small, and therefore lightweight and relatively inexpensive. For example, a preferred distance between any transmitter and the receiver is approximately two feet.

It should be noted that all three preferred embodiments are adaptable to be portable. For example, the open transmitters and tubed transmitters can be coupled to foldable lightweight legs that fold open and closed for transporting by a person.

It should be noted that in the open configuration, the receiver is sufficiently sensitive to receive the ultrasonic pulses.

It should be noted that a preferred material for the ventilated tube is a lightweight plastic protective material.

It should be noted that in all three preferred embodiments, the measurements taken are digital, as opposed to analogue, and are therefore more accurate.

It should be noted that in all three preferred embodiments, there are no moving parts to make the invention, for example, cumbersome, and to be distracting to a user.

Accordingly, although the invention has been described in detail with reference to three particular preferred embodiments, persons possessing ordinary skill in the art to which this invention pertains will appreciate that various modifications and enhancements may be made without departing from the spirit and scope of the claims that follow.

What is claimed is:

1. A process for calculating a gas velocity vector in standard atmospheric pressure, the process comprising:

providing a first transmitter element adapted to transmit ultrasonic pulses, a second transmitter element adapted to transmit ultrasonic pulses and a receiver element adapted to receive ultrasonic pulses, whereby said first transmitter is positioned a first distance from said receiver, said second transmitter is positioned a second distance from said receiver and positioned at a 90 degree angle from and coplanar with said first transmitter;

transmitting a first ultrasonic pulse from said first transmitter to said receiver and calculating a first transit time for said first pulse to reach said receiver;

transmitting a second ultrasonic pulse from said second transmitter to said receiver and calculating a second transit time for said second pulse to reach said receiver;

calculating a first transit time differential vector by determining a first difference between said calculated first transit time and a first predetermined transit time of an ultrasonic pulse transmitted from said receiver to said first transmitter in standard atmospheric pressure;

calculating a second transit time differential vector by determining a second difference between said calculated second transit time and a second predetermined transit time of an ultrasonic pulse transmitted from said receiver to said second transmitter in standard atmospheric pressure; and determining said gas velocity vector by combining said first transit time differential vector and said second transit time differential vector.

2. The process of claim 1, wherein said first transmitter, said second transmitter, and said receiver are adapted to be portable.

3. The process of claim 1, wherein said first transmitter comprises an ultrasonic piezoelectric transducer and said second transmitter comprises an ultrasonic piezoelectric transducer.

4. An apparatus for calculating a gas velocity vector in standard atmospheric pressure, the apparatus comprising:

a first transmitter element adapted to transmit ultrasonic pulses, a second transmitter element adapted to transmit ultrasonic pulses, a receiver element adapted to receive ultrasonic pulses, whereby said first transmitter is positioned a first distance from said receiver, said second transmitter is positioned a second distance from said receiver and positioned at a 90 degree angle from and coplanar with said first transmitter;

means for transmitting a first ultrasonic pulse from said first transmitter to said receiver and calculating a first transit time for said first pulse to reach said receiver;

means for transmitting a second ultrasonic pulse from said second transmitter to said receiver and calculating a second transit time for said second pulse to reach said receiver;

means for calculating a first transit time differential vector by determining a first difference between said calculated first transit time and a first predetermined transit time of an ultrasonic pulse transmitted from said receiver to said first transmitter in standard atmospheric pressure;

means for calculating a second transit time differential vector by determining a second difference between said calculated second transit time and a second predetermined transit time of an ultrasonic pulse transmitted from said receiver to said second transmitter in standard atmospheric pressure; and means for determining said gas velocity vector by combining said first transit time differential vector and said second transit time differential vector.

5. The apparatus of claim 4, wherein said first transmitter, said second transmitter, and said receiver are adapted to be portable.

6. The apparatus of claim 4, wherein said first transmitter is an ultrasonic piezoelectric transducer and said second transmitter is an ultrasonic piezoelectric transducer.

* * * * *